US00PP16594P3

(12) United States Plant Patent
Castillo Pimentel

(10) Patent No.: US PP16,594 P3
(45) Date of Patent: May 30, 2006

(54) AVOCADO TREE NAMED 'CARLA'

(50) Latin Name: *Persea americana*
Varietal Denomination: Carla

(75) Inventor: Carlos Antonio Castillo Pimentel, Santo Domingo (DO)

(73) Assignee: Agroindustria Ocoeña, S.A., Santo Domingo (DO)

( * ) Notice: Subject to any disclaimer, the term of this patent is extended or adjusted under 35 U.S.C. 154(b) by 128 days.

(21) Appl. No.: 10/889,332

(22) Filed: Jul. 12, 2004

(65) Prior Publication Data

US 2006/0010540 P1 Jan. 12, 2006

(51) Int. Cl.
*A01H 5/00* (2006.01)

(52) U.S. Cl. ..... Plt./200

(58) Field of Classification Search ..... Plt./200
See application file for complete search history.

*Primary Examiner*—Kent L. Bell
*Assistant Examiner*—W. C. Haas
(74) *Attorney, Agent, or Firm*—Lott & Friedland, P.A.

(57) ABSTRACT

A new and distinct variety of *Persea americana* is disclosed. A vigorous moderately-spreading upright growth habit is exhibited. The tree starts blooming in mid-March and the blooms are of the "B" type. The fruit is harvested from late February through May. The fruit is elliptical-spheroid obliquely toward apex on one side, occasionally fruit have a raised ridge, chimera, running along a side from the stem down. The fruit skin is a dark green, nearly smooth. This fruit has good to excellent quality flesh.

14 Drawing Sheets

Latin name of the genus and species of the plant claimed: *Persea americana.*
Varietal denomination: 'Carla'.

BACKGROUND OF THE INVENTION—DISCOVERY AND ASEXUAL REPRODUCTION OF THE TREE

This invention relates to a new and distinct variety of Avocado tree (*Persea americana*), denominated 'Carla'.

The 'Carla' tree was discovered in 1994 as a single plant in the inventor's orchard in the Ocoa River valley of the Dominican Republic. Had the new variety not been discovered and preserved it would have been lost to mankind.

'Carla' was first asexually propagated in 1994 by grafting budwood onto rootstocks in the inventor's nursery in Ocoa, Dominican Republic, and directly in the inventor's orchards in the Ocoa River Valley, Dominican Republic. This and subsequent asexual propagation has confirmed that the new variety is stable and that the progeny are formed true to type.

SUMMARY OF THE TREE

'Carla' is a Guatemalan×West Indian hybrid, seedling of unknown parentage. It was discovered as a precocious and consistent fruit setting seedling tree.

'Carla' has several unique and distinguishing characteristics which make it commercially valuable. It is the only West Indian variety that matures in late February known to the inventors and can be harvested through May. Through experimentation it has been demonstrated that with proper irrigation the fruit will hang from the trees through the month of June. No West Indian varieties known to the inventors of avocado fruit are harvested during this time period. The West Indian avocado harvest season generally extends from mid-May to March, with the peak production period being from July through December.

Fruit is of large size and with good to excellent quality. The fruit oil content is 8% to 13%. The fruit flesh does not readily oxidize when cut. Flesh discoloration beings to occur 24–48 hours after the fruit is cut. The fruit is fairly cold tolerant and can be stored at 7.2° C. to 7.5° C. and 90% relative humidity for several weeks. The fruit has been shipped to Puerto Rico and the east coast of the United States without any post harvest problems. As the young orchards come into heavier production the use of cold storage could possibly extend the sales season for this variety through July.

'Carla' can be distinguished from all previously known avocado varieties in view of its distinctive combination of characteristics. 'Carla' is believed to be well suited for production of quality avocados under commercial growing conditions. Observations of the new 'Carla' tree may be made at the inventor's orchard in the Ocoa River valley of the Dominican Republic.

BRIEF DESCRIPTION OF THE FIGURES

The accompanying photographic illustrations show typical specimens of the vegetative growth and flowers of the new variety in different stages of development and depicted in color as nearly true as it is reasonably possible.

DETAILED BOTANICAL DESCRIPTION OF THE TREE

Figure 1:
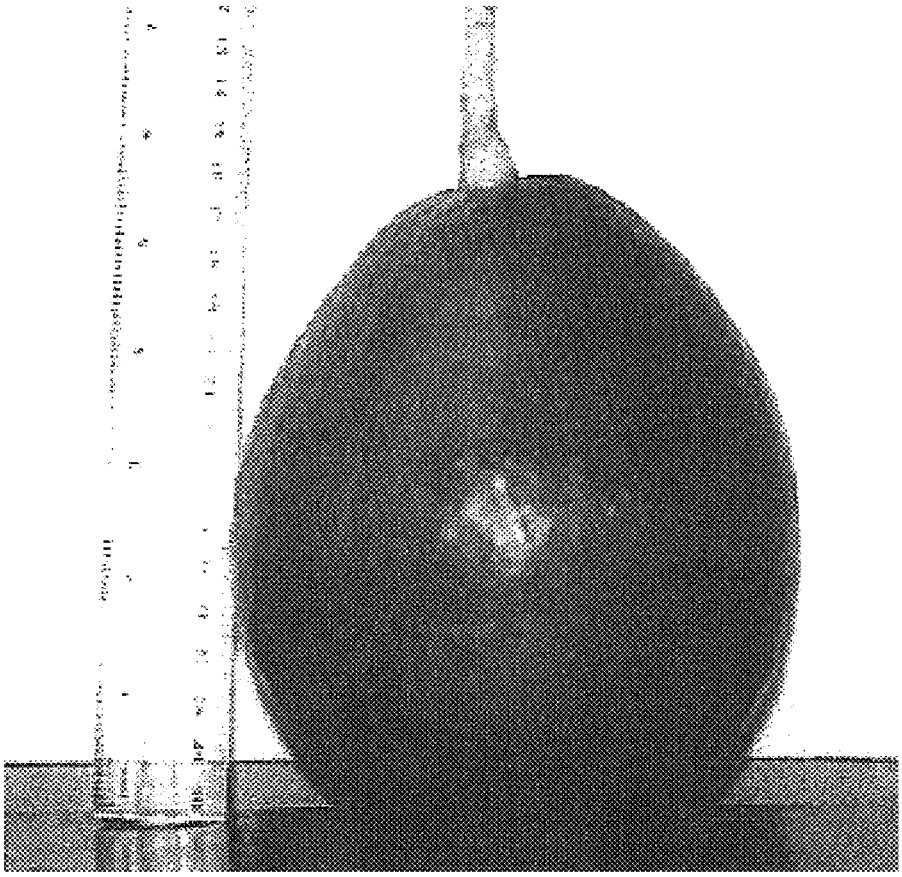
FIG. 1 illustrates an exterior view of the typical mature fruit of the new variety.
Figure 2:
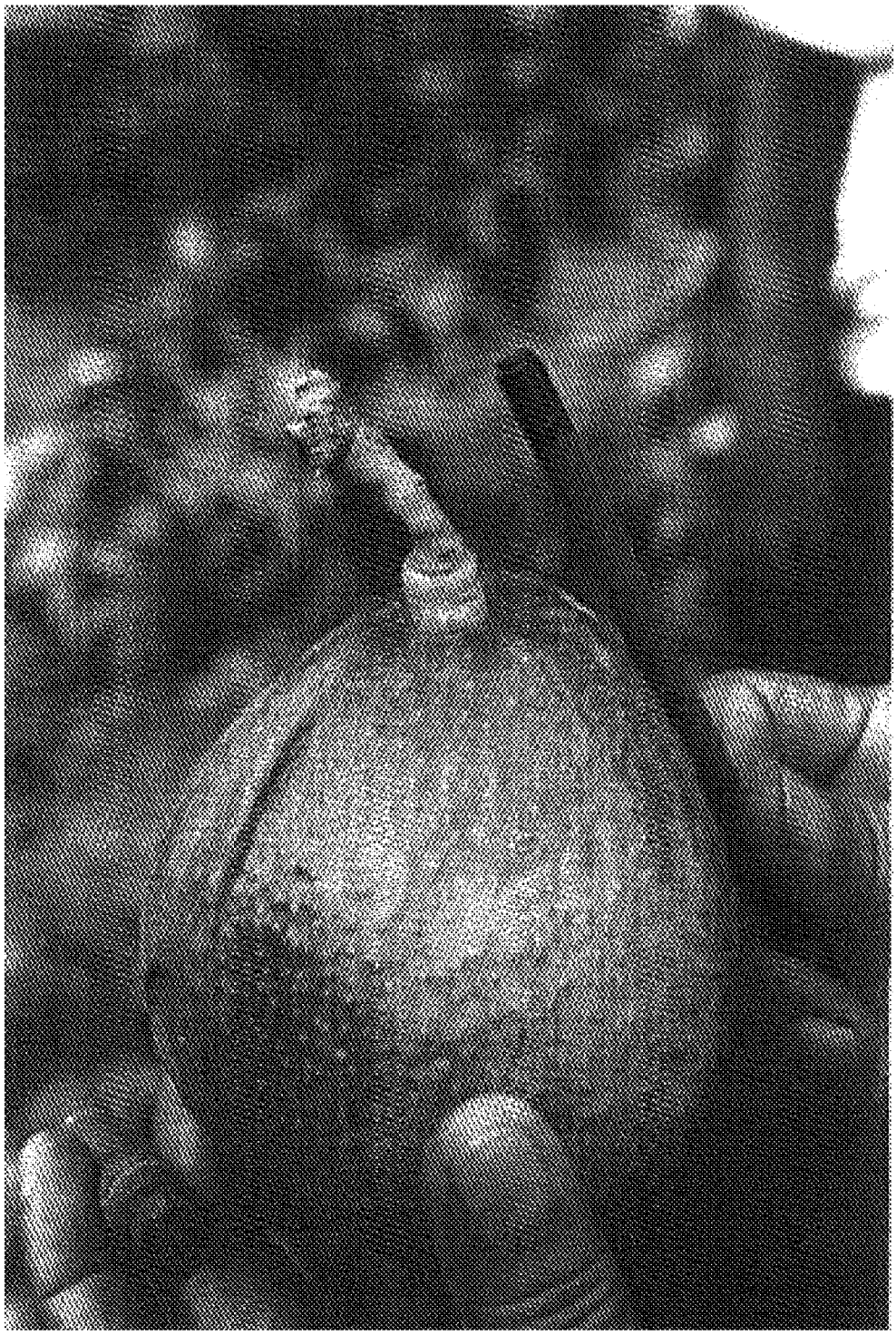
FIG. 2 illustrates an exterior view of the mature fruit of 'Carla' with the chimera, ridge running from the stem down the side.
Figure 3:
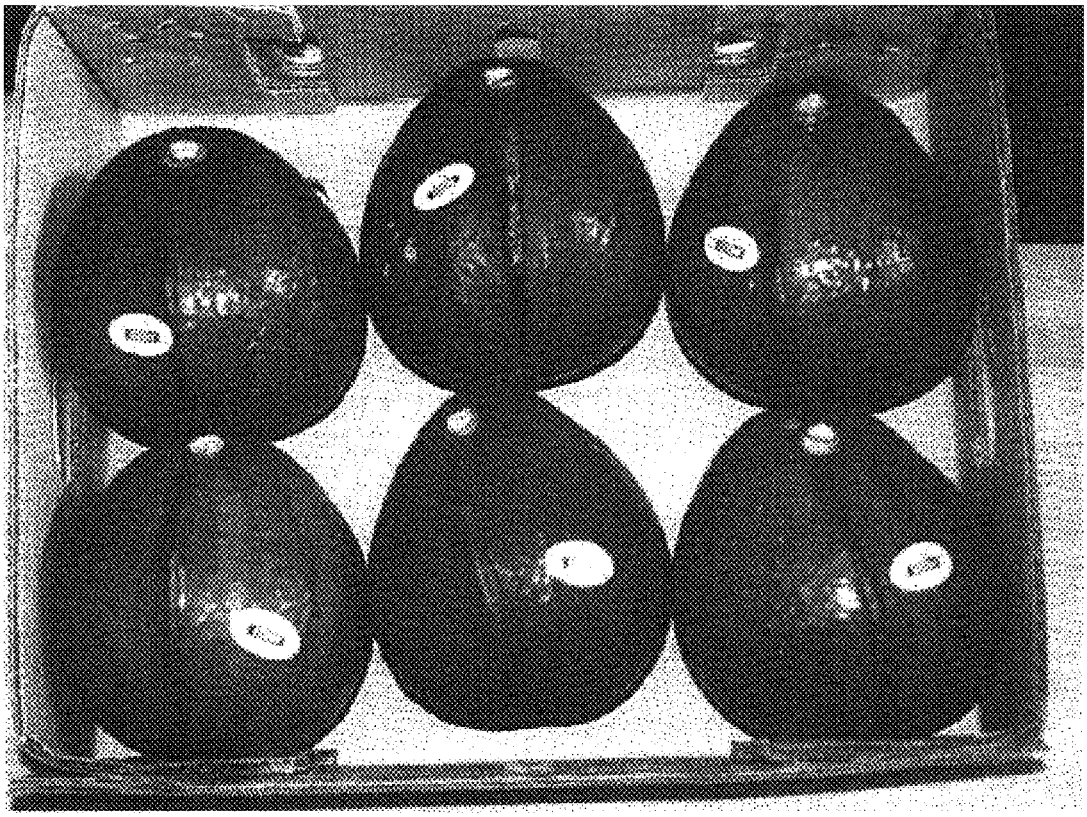
FIG. 3 illustrates a box of 'Carla' fruit with the raised chimera.
Figure 4:
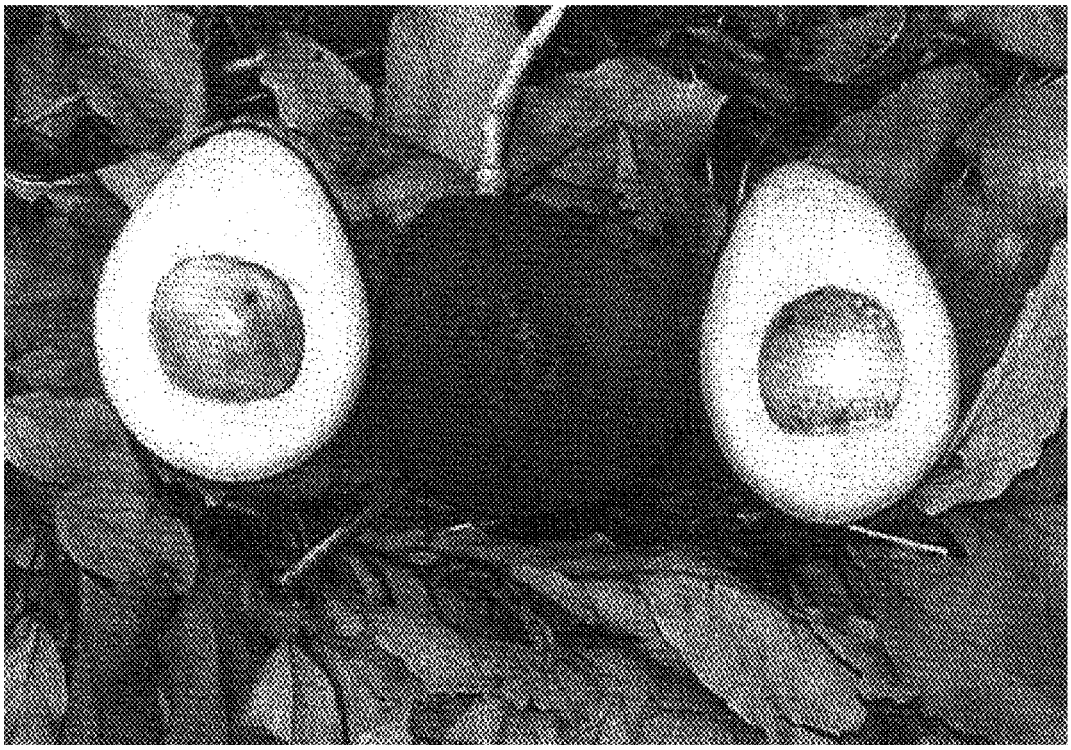
FIG. 4 illustrates a sagittal section of the fruit with the seed intact.
Figure 5:
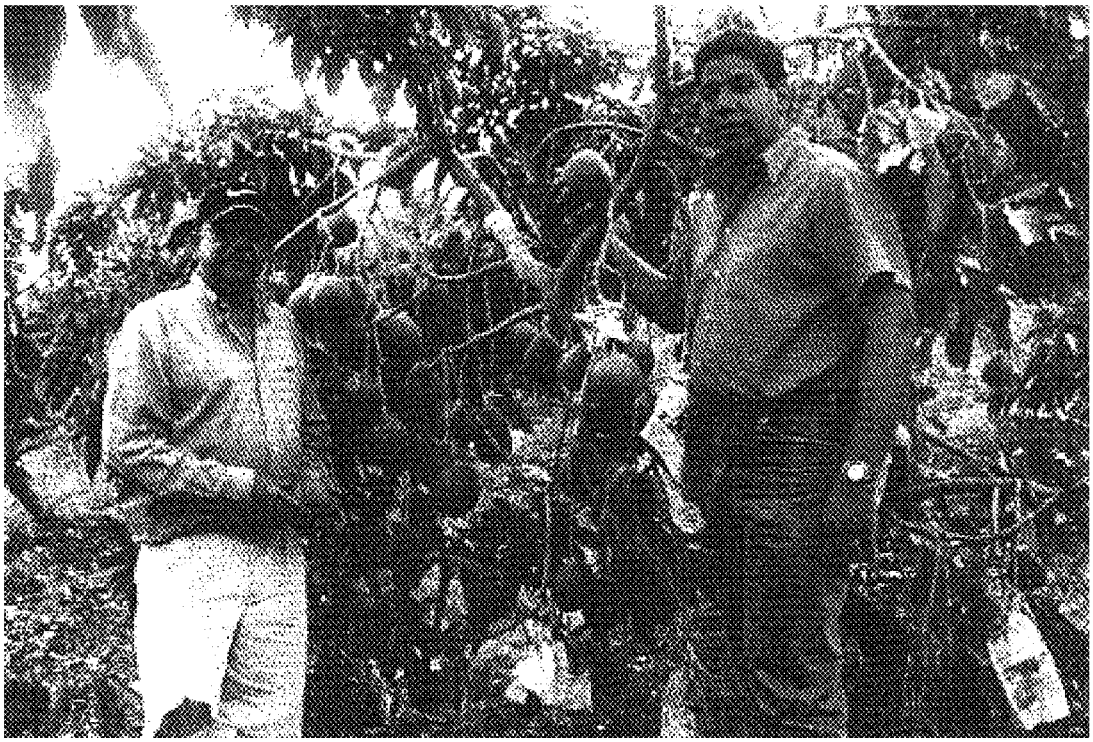
FIG. 5 illustrates a fruit laden 4 year old 'Carla' tree with the inventor (L) and his son (R), Karel Castillo standing next to it for scale reference. The tree is approximately 6 feet tall and shows typical growth pattern for the new variety.
Figure 6:
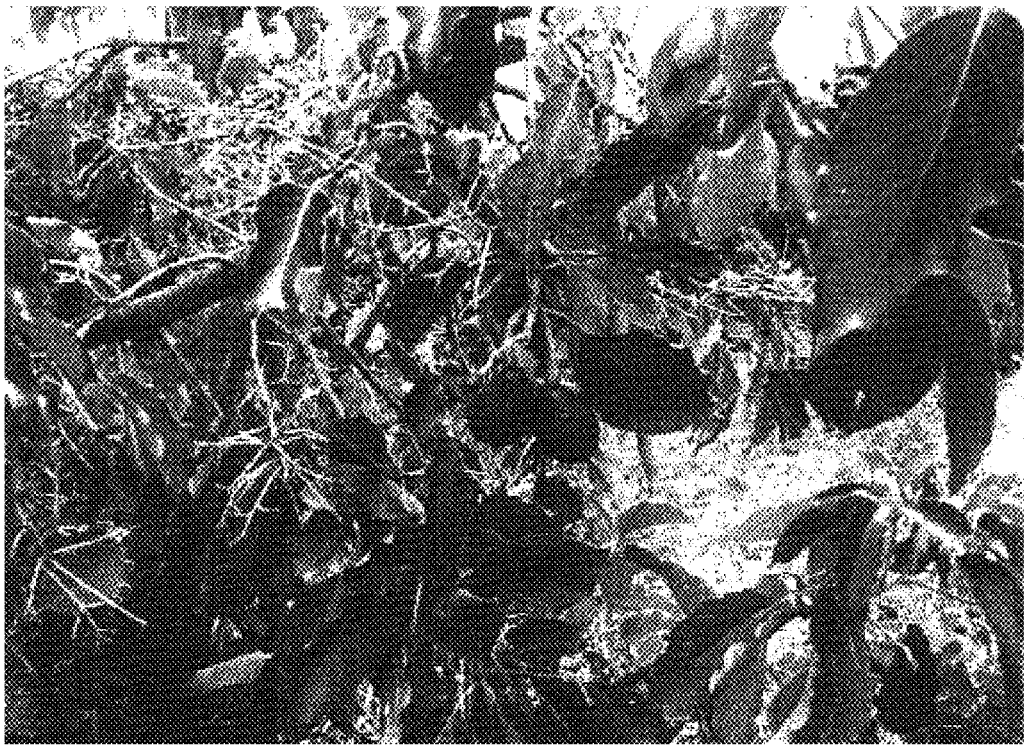
FIG. 6 illustrates different sizes of fruit for the 'Carla' Avocado in early June 2004. Largest fruit was set in March 2004.
Figure 7:
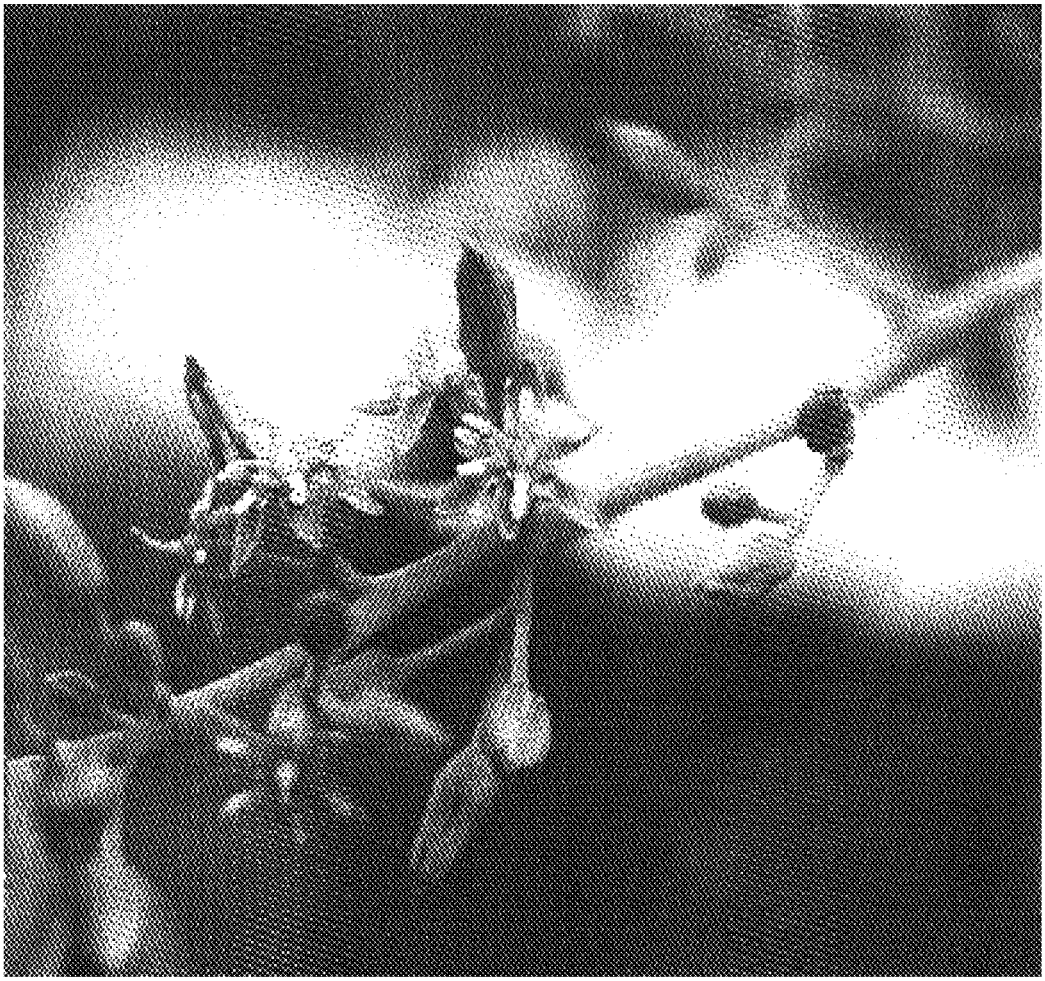
FIG. 7 illustrates flowers in the female stage of the 'Carla' avocado in normal bloom in the Ocoa River valley of the Dominican Republic. Flower type is "B."
Figure 8:
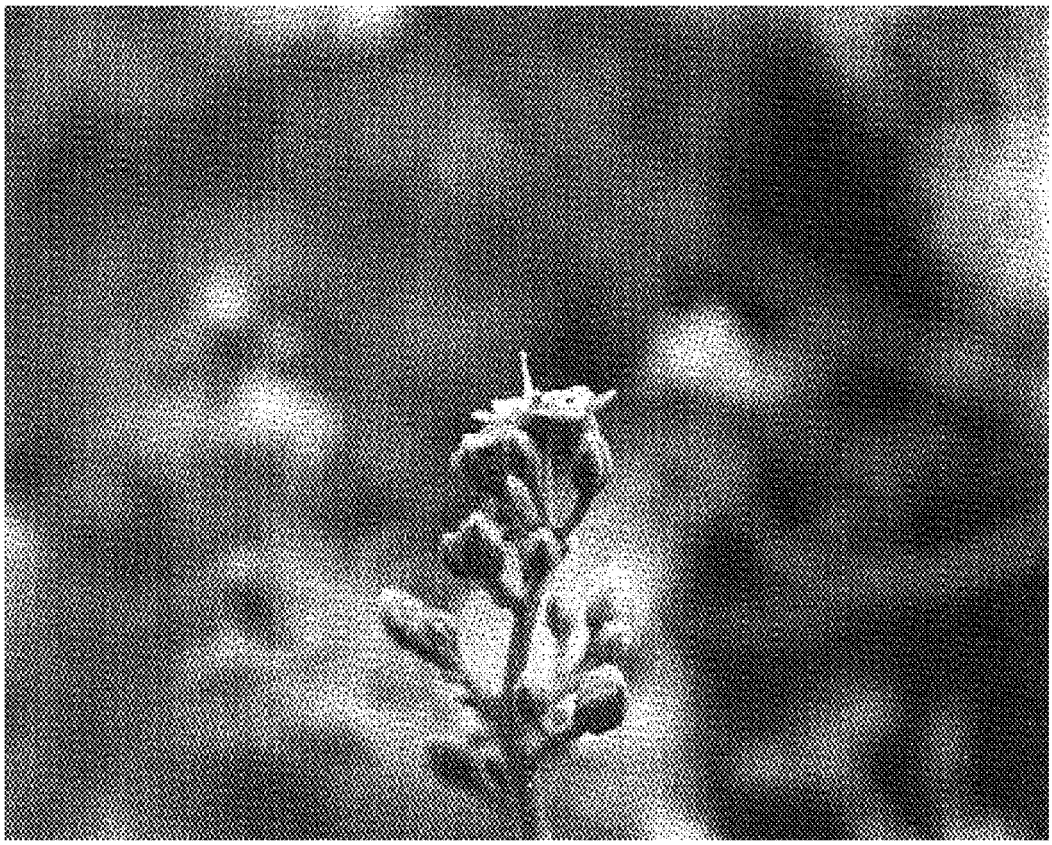
FIG. 8 illustrates the distinct pistil of the female stage of the Carla avocado flower in the Ocoa valley of the Dominican Republic. Flower type is "B".
Figure 9:
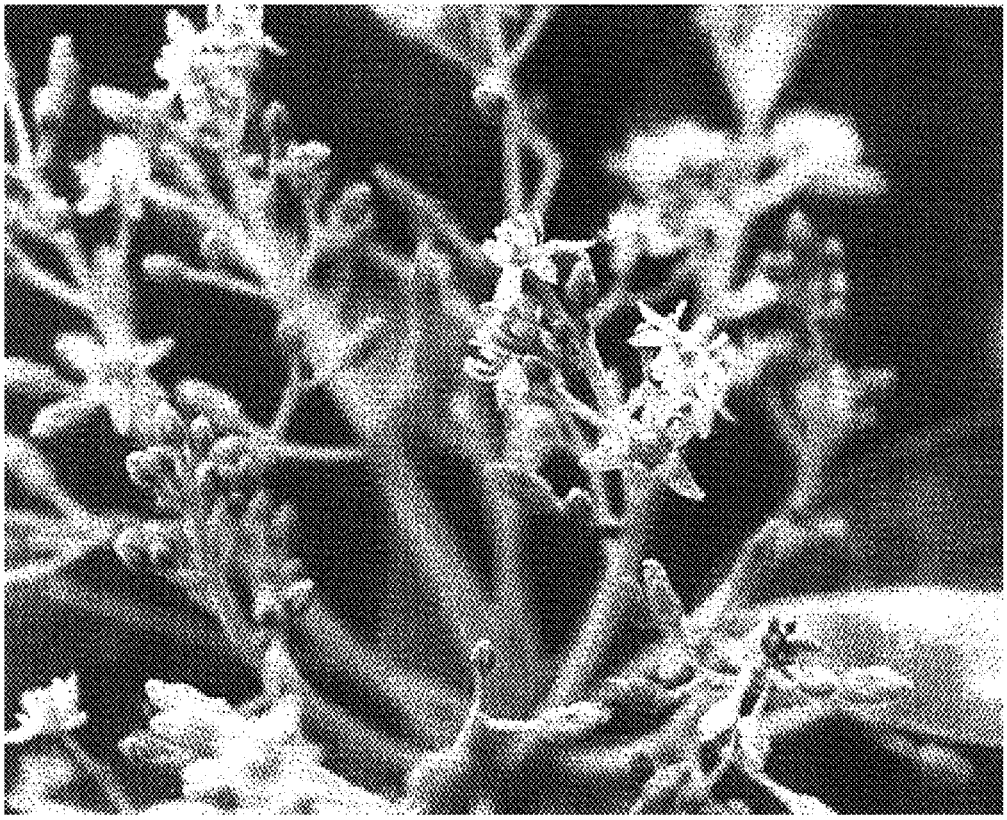
FIG. 9 illustrates a panicle flowers in the distinct male stage of the 'Carla' avocado in normal bloom in the Ocoa River valley of the Dominican Republic. Flower type is "B."
Figure 10:
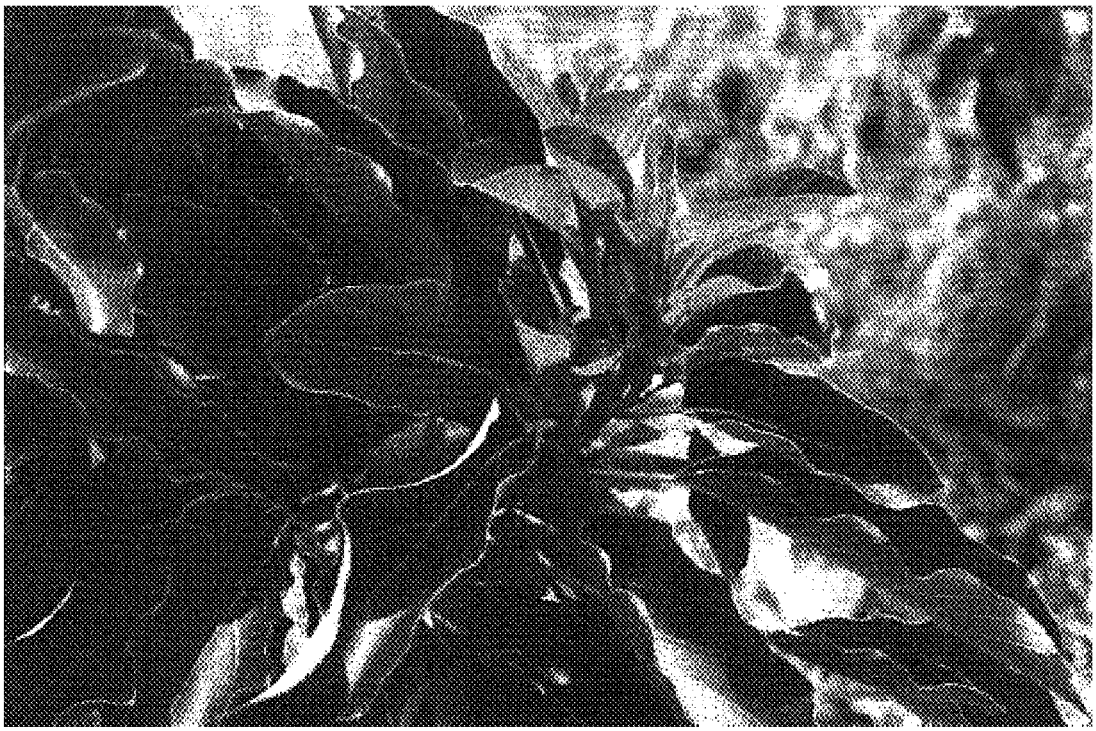
FIG. 10 illustrates young leaves of the 'Carla' variety exhibiting the anthocyanin color on the young shoots and developing leaves. Mature leaves in background.
Figure 11:
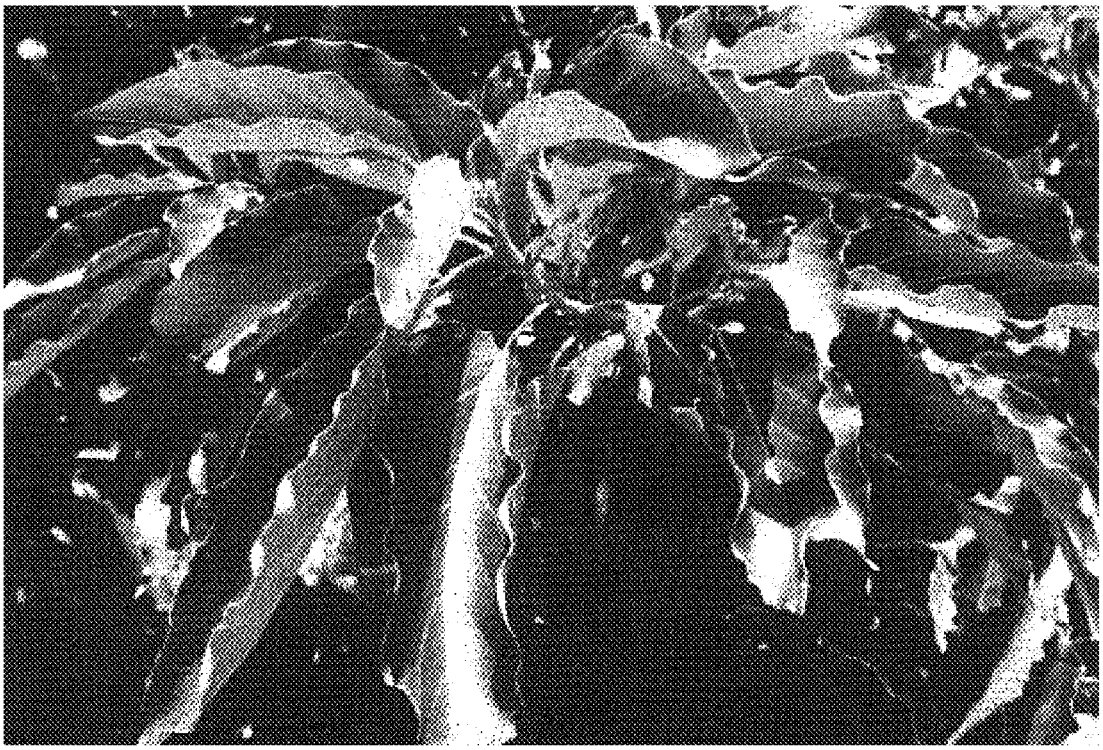
FIG. 11 illustrates mature lanceolate shape leaves with pinnate venation.
Figure 12:
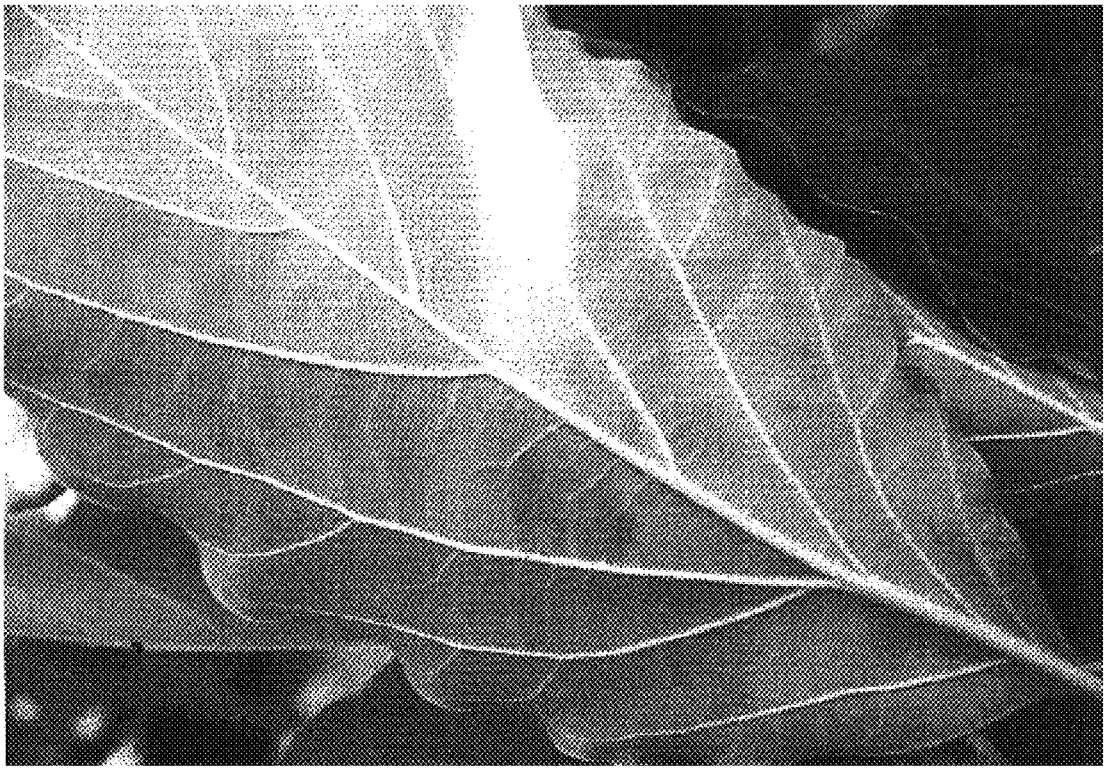
FIG. 12 illustrates the grayish-green underside of a mature leaf with pinnate venation.
Figure 13:
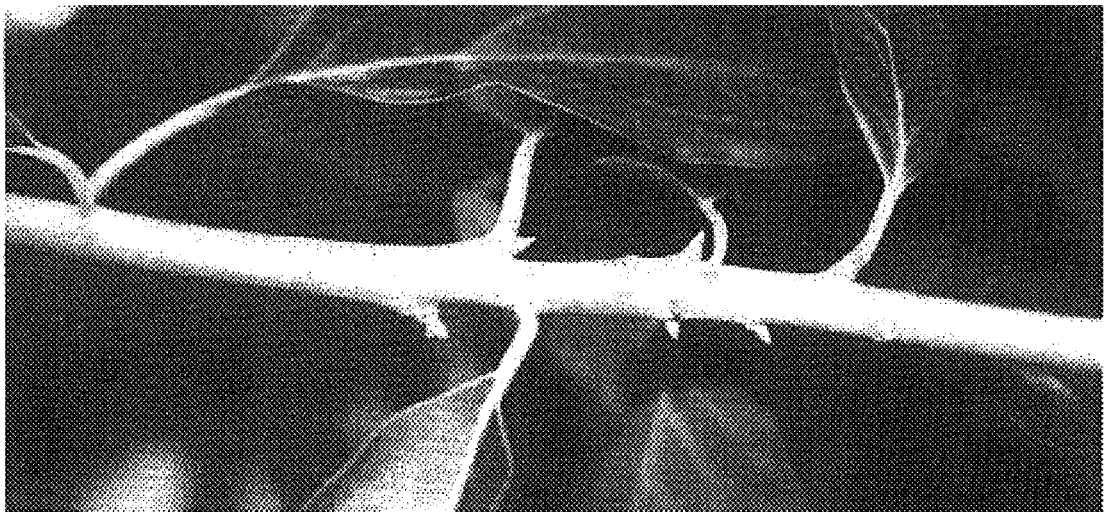
FIG. 13 illustrates small branch with the lanceolate buds of the 'Carla' variety.
Figure 14:
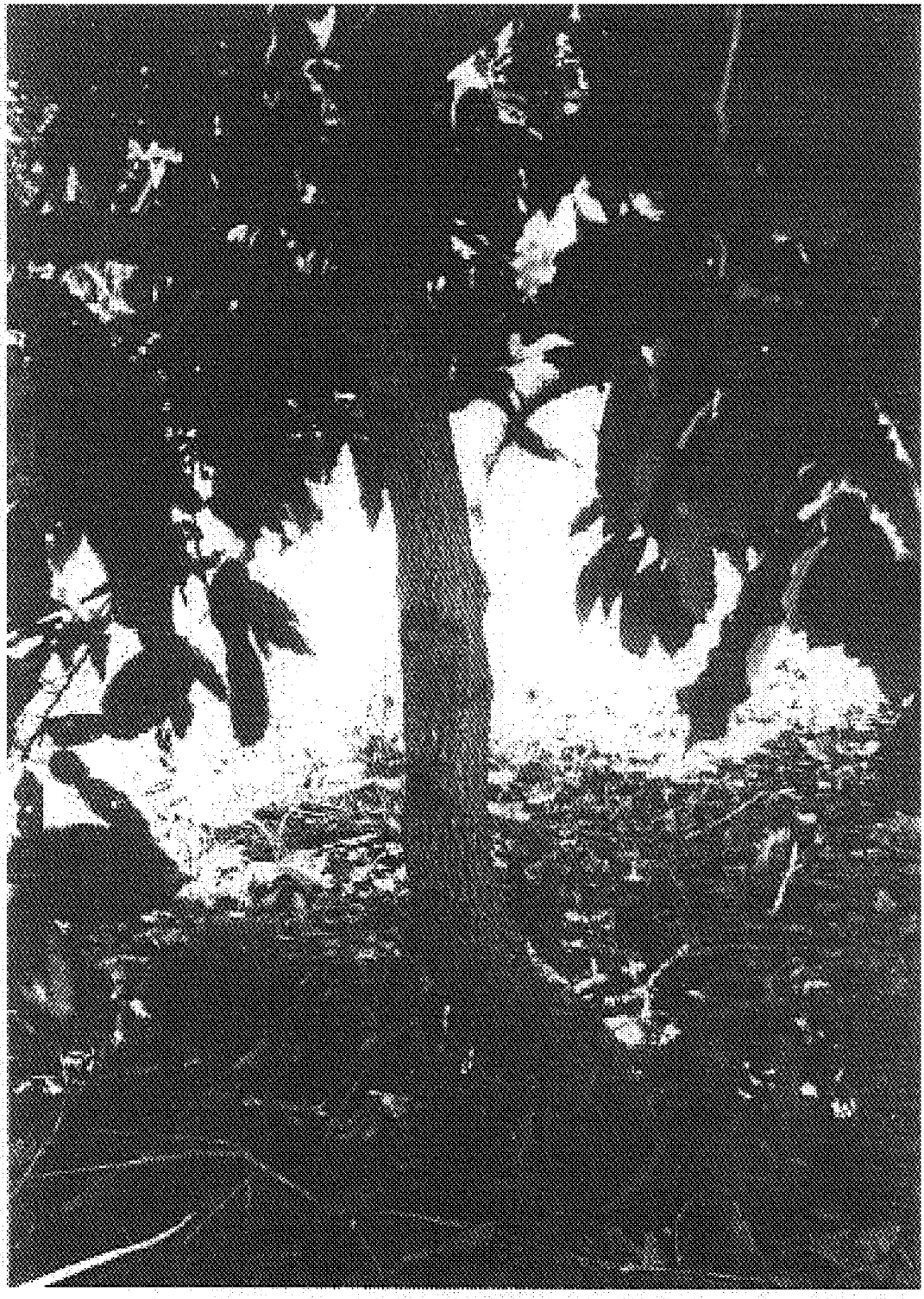
FIG. 14 illustrates the trunk of the 'Carla' avocado with the typical avocado bark.

The following is a detailed botanical description of the tree of the present invention. The trees are being grown and propagated in the Ocoa Valley region of the Dominican Republic. The trees being described were approximately 6 years of age at the time of photographing, and have been grafted on *Persea americana* seedling rootstocks. The rootstocks are of the Guatemalan×West Indian cultivars.

Color references are to The R.H.S. Colour Chart of The Royal Horticultural Society, London, England. Where appropriate, general color terms are used in accordance with the ordinary dictionary.

Tree:

*Growth habit.*—A vigorous moderately-spreading upright growth habit is exhibited.

*Height.*—The trees are maintained at a height of 3.5 meters to 4.5 meters. Orchard trees in tropical areas can reach heights as high as 15 to 25 meters. However, they are generally maintained at much lower heights, 3 to 7 meters via topping and pruning.

*Width.*—Approximately 3 meters on average. The diameter is controlled by pruning.

*Bark.*—New wood is normal green, smooth bark, without corky or specially pigmented lenticels. Old wood is similar to most avocado varieties. Mature bark is Grayed-Green Group 196A in coloration.

*Trunk size.*—Approximately 10 cm to 15 cm in diameter at 30 cm to 40 cm high. However, this will vary greatly among the trees because the understock (rootstocks) used will vary in their growth pattern.

Foliage:

*Leaf arrangement.*—The leaves are alternate and entire with a rounded base.

*Young leaves.*—Anthocyanin is present in young stems and leaves, varying from light to moderate.

*Mature leaves.*—Large size, shape is lanceolate with an acute point. The margins of the leaves are entire with wavy margins.

*Leaf length.*—Average length is 250 mm, range 190 mm to 320 mm.

*Leaf width.*—Narrow to wide, average width is 90 mm, range 70 mm to 130 mm.

*Leaf tip.*—Acute, anthocyanin present in newly emerged leaves, anise aroma not present when crushed.

*Leaf margin.*—Entire and wavy.

*Leaf texture.*—Pubescent when young becomes smooth and leathery when mature.

*Leaf color.*—Upper surfaces of mature leaves are Yellow-Green Group 139A in coloration. Lower surfaces are Yellow-Green Group 137C in coloration. Leaf color can vary with leaf age, location on the tree, light exposure and individual nutrition.

*Leaf venation pattern.*—Pinnate leaf venation pattern.

*Leaf vein color.*—Yellow-Green Group 144 D to 145 A.

*Petiole length.*—Average length is 47 mm, range 35 mm to 44 mm.

*Petiole diameter.*—Average diameter is 3.4 mm, range 3.8 mm to 4.5 mm.

*Petiole color.*—Color is near Yellow-Green Group 145A. Color range Yellow-Green Group 145A to 145D).

Inflorescence:

*Flower type.*—Type "B". Flowers exhibit a unique behavior described as "protogynous dichogamy with synchronous daily complementarity" and are borne in panicles. A single tree may have hundreds of panicles, each potentially with hundreds or thousands of flowers. A mature tree may have a million flowers.

*Opening.*—Flowers start opening as a female flower late morning to early afternoon. The male flower opens the next morning; the flower's cycle last 20 to24 hours. The flowering behavior is commonly observed when climatic conditions are ideal but the cycle may be disrupted, particularly by cool temperatures.

*Reproductive organs.*—The reproductive organs consist of nine (9) fertile stamens each having four (4) pollen chambers and two (2) basal orange nectar glands, three (3) staminodia are present; anthers tetrathecal; ovary pubescent. The single pistil has one (1) carpel with one (1) ovule.

*Bud shape.*—Lanceolate to oblong-lanceolate, rounded base, acute tip.

*Bud size.*—Bud length varies between 8 and 9 mm. Bud width averages 4 mm.

*Petal.*—Petals are Green-Yellow Group 151A in coloration, average length is about 6 mm; average width about 2 mm; margins are smooth and uniform, texture is smooth; densely silky-tomentose on both surfaces. Shape is apex acute, base flattened.

*Pedicel.*—Pedicels are Green-Yellow Group 151A in coloration. Average length about 5 mm to 6 mm; width about 1 mm to 2 mm; average diameter about 1 mm.

Fruit (mature):

*Shape.*—Early maturing, size large to very large. Shape is obovate-spheroid, fruit apex is rounded, asymmetrical pedicel insertion, bottom of fruit is somewhat flattened. Occasionally fruit have a raised ridge, chimera, running along a side from the stem down.

*Pedicel.*—Average length 11 mm, range 8 mm to 15 mm. Average diameter 13.5 mm, range 12 mm to 15.5 mm. Coloration is Yellow-Green Group N144A. Color range is Yellow-Green Group N144A to N151D.

*Peduncle.*—Average length 85 mm, range 40 mm to 150 mm. Color Yellow-Green Group N144A. Color range Yellow-Green Group N144A to N151D.

*Fruit size.*—Typical mature fruit length 130 mm, range 120 mm to 140 mm. Typical mature fruit diameter 120 mm, range 110 mm to 130 mm.

*Fruit weight.*—Typical mature fruit weight averages 920 g.

*Fruit skin.*—Typical fruit skin color is Yellow-Green Group 147 B to C. Skin texture is smooth to slightly rough and cuts easily. Fruit skin diameter is relatively thick.

*Fruit flesh color.*—Yellow-Green Group 153C.

*Fruit weight.*—Average fruit weight 920 g, range 425 g to 1243 g. The fruit weight will depend on the crop load of the trees and whether the fruit is allowed to hang longer on the trees.

*Seed.*—Medium to large size, fits tightly into the cavity. Shape is longitudinal section, base flattened, ovate, apex conical. Weight about 45 g, range 39 g to 50 g. Length is about 45 mm, range 42 mm to 46 mm. Diameter averages 55 mm, range 52 mm to 58 mm. Color of seed coat Grayed Orange Group 166D. The cotyledon color is Orange White Group 159C.

*Flesh.*—Texture is smooth with fibers in flesh inconspicuous.

Productivity: 'Carla' allows trees to set heavy. Trees consistently bear relatively large amounts of fruit. The trees under observation have never failed to set a large crop.

Market use: The fruit is well suited for the fresh retail and food service markets. The large size of the fruit makes it uniquely suitable for restaurant and food service markets. The fruit has good to excellent flavor and it has the unusual characteristic of not oxidizing after it has been cut in half. The flesh will not discolor when left in the open for up to six (6) to eight (8) hours. When refrigerated the cut fruit maintains it color without discoloring for over 48 hours giving it excellent storability and suitability to environments where the consumer does not intend to use entire fruit at one time.

The fruit can be stored at 7.2° C. to 7.5° C. and +90% relative humidity, for several weeks without any internal breakdown. Natural ripening occurs five (5) to eight (8) days after harvesting.

'Carla' has pick dates from February through early June without significant market competition from any other West Indian variety. Its ability to withstand long term cold storage reasonably enables sales into the month of July. The inventor is not aware of any variety of avocado tree in the Dominican Republic, other than 'Carla', that has consistently produced fruit of marketable size and weight which can be harvested as late as March through June. This characteristic renders 'Carla' unique and patentable.

The relatively thick skin gives good protection to the flesh when it is being handled, either by picking, washing, packing or transporting. Fruit texture makes it suitable for use in place of butter, a common use of the avocados since it has no cholesterol and is plentiful in natural oils that are beneficial to the consumer's health. The 'Carla' fruit is suitable for use in fresh salads, guacamole, dips, sauces and other avocado by-products.

I claim:

1. A new and distinct variety of avocado tree substantially as herein shown and described.

* * * * *